United States Patent [19]
Howell

[11] Patent Number: 5,197,958
[45] Date of Patent: Mar. 30, 1993

[54] WETNESS INDICATING DIAPER

[76] Inventor: Wesley A. Howell, 6926 Doheny, Unit D, Alto Loma, Calif. 91701

[21] Appl. No.: 861,475

[22] Filed: Apr. 1, 1992

[51] Int. Cl.$^5$ .............................................. A61F 13/15
[52] U.S. Cl. ................................... 604/361; 604/385.1
[58] Field of Search ...................... 604/358, 361, 385.1

[56] References Cited

U.S. PATENT DOCUMENTS

| | | | |
|---|---|---|---|
| 3,794,024 | 2/1974 | Kokx et al. | 604/361 |
| 3,955,575 | 5/1976 | Ookuda . | |
| 4,192,311 | 3/1980 | Felfoldi | 604/361 |
| 4,231,370 | 11/1980 | Mroz et al. | 604/372 X |
| 4,327,731 | 5/1982 | Powell | 128/287 |
| 4,356,818 | 11/1982 | Macias et al. | 604/361 X |
| 4,507,121 | 3/1985 | Leung | 604/361 |
| 4,516,975 | 5/1985 | Mitchell . | |
| 4,568,342 | 2/1986 | Davis . | |
| 4,653,491 | 3/1987 | Okada et al. | 128/886 |
| 4,705,513 | 11/1987 | Sheldon et al. | 604/361 |
| 4,735,622 | 4/1988 | Acuff et al. | 604/385.1 X |
| 5,066,711 | 11/1991 | Colon et al. | 604/361 X |
| 5,078,708 | 1/1992 | Haque | 604/361 |

Primary Examiner—Randall L. Green
Assistant Examiner—Mary Beth O. Jones
Attorney, Agent, or Firm—Knobbe, Martens, Olson & Bear

[57] ABSTRACT

The present invention is a reusable wetness indicating cloth diaper which uses a thermally sensitive indicator to indicate that the diaper has become soiled. The diaper of the present invention includes material which at least partially thermally insulates the outer surface from said inner surface and an indicator on the outer surface which provides a visual indication when the outer surface has a temperature above a given threshold. The temperature threshold is chosen such that the visual indication will generally not be present when a baby wearing said diaper is dry, but will generally be present when the baby secretes waste material into the diaper. A thermochromic ink indicates a temperature change in the diaper. A plurality of discrete indicators are distributed over substantially the entire outer surface of the diaper with the indicators forming a repeating pattern. Desirably, the indicators cover a significant portion of the outer shell of the diaper so that the wetness condition can be easily detected from most viewing angles of the diaper in an aesthetically pleasing manner.

23 Claims, 3 Drawing Sheets

WETNESS INDICATING DIAPER

BACKGROUND OF THE INVENTION

The present invention generally relates to diapers and, in particular, to diapers which indicate when the diaper is wet.

The concept of a wetness indicating diaper is known in the diaper art, but the various attempts at achieving this have been quite cumbersome. Some of the prior art wetness indicators are located at a single location on the diaper. Therefore, various wicking methods are required to move the wetness from its original location on the diaper to the indicator location to react with the indicating substance to signal that the diaper is wet. The prior art diapers are particularly unadvantageous when the original wetting location is significantly far from the indicator location and the amount of wetness is not substantial. In this case, the limited amount of wetness, if any, that reaches the indicator may not be enough to trigger the indicating means.

In addition, the single location indicators of the prior art are often located at either the bottom or top of the diaper and, depending on the type of outfit that the baby is wearing, can be difficult to read when the baby is fully clothed. In many cases, the baby has to be virtually undressed to find the indicator mark, thus greatly limiting the utility of a wetness indicator. Furthermore, these single location indicators are not aesthetically pleasing.

Other prior art wetness indicators have utilized complex electronic circuitry t detect moisture in the diapers such as U.S. Pat. No. 4,356,818, issued to Macias, et al. In the Macias, et al. patent, the presence of moisture causes two isolated conduits to short circuit, and thus indicate that the diaper is wet. A detector and an indicator means have to be hooked up to the conduit to signify when the short circuit condition occurred, and therefore that the diaper is wet. These electronic wetness detectors are elaborate designs which require the addition of multiple components to the assembly and use of the diaper. In addition, placing electronics in a diaper for use with a child is undesirable, as mothers may fear possible electrocution of the child, even if this is not feasible.

Many of the prior art wetness indicating systems are designed for disposable diapers, therefore the wetness indicator systems are only intended for single use applications. These single use systems for disposable lo diapers can not be used in cloth diapers which, after soiling, are washed, dried and then reused. Due to the added cost to the diaper as a result of the wetness indicating system, it is desirable that the diaper be reusable from a cost efficiency standpoint.

A reusable cloth diaper needs a wetness indicating system that after drying will reindicate a dry condition and then reindicate a wet condition when the diaper is again wet. In contrast, most of the disposable indicating systems of the prior art cannot be reused. In addition, the prior art wetness indicating systems are generally not durable enough to withstand the continual washings of the cloth diaper. The washing process repeatedly subjects the diapers to detergents and heat, and the indicating systems of the prior art are not able to withstand these harsh environments.

Finally, the disposable diapers of the prior art are not reusable and therefore not recyclable. With the current heavy burden on the landfills in this country, a reusable diaper that is easy to use, and commercially appealing is needed. For these and other reasons, the wetness indicating diapers of the prior art have not gained widespread acceptance, therefore there exists a need for an improved wetness indicating reusable diaper.

SUMMARY OF THE INVENTION

The present invention is a reusable wetness indicating cloth diaper which uses a thermally sensitive indicator to indicate that the diaper has become soiled. The diaper of the present invention comprises an inner surface adapted to be positioned against the skin of a baby, an outer surface generally opposed to the inner surface adapted to form the exterior of the diaper, material which at least partially thermally insulates the outer surface from the inner surface and an indicator on the outer surface which provides a visual indication when the outer surface has a temperature above a given threshold. The temperature threshold is chosen such that the visual indication will generally not be present when a baby wearing the diaper is dry, but will generally be present when the baby secretes waste material into the diaper. The material of the diaper when dry is insufficiently thermally conductive for a normal body temperature to raise the outer surface above a given threshold but is sufficiently thermally conductive when wet to raise the outer surface temperature above a given threshold. More specifically a layer of the material provides at least some thermal insulation capacity when dry and a lower thermal insulation capacity when wet. In addition, the material of the diaper is provided to wick the moisture secreted from the baby toward the outer layer to further assist in the indication of wetness.

The preferred construction of the diaper comprises an outer shell having a front portion, a back portion and a connecting portion extending between the front and back portions, an inner pad attached to the outer shell solely at the front portion and the back portion, and an indicator on the outer shell which provides a visual indication when the outer shell has a temperature above a given threshold. The inner pad defines an inner surface adapted to be positioned against the skin of a baby when the diaper is worn, and, when dry, at least partially thermally insulates the inner surface from the outer shell. The inner pad has a thickness of at least ⅜ of an inch and further comprises a sorbent layer, a protective cover defining the inner surface of the diaper, and a layer of wicking material between the protective cover and the sorbent layer. The protective cover surrounds the sorbent layer, thereby separating the sorbent layer from the outer shell.

The cloth of the diaper is sufficiently durable to withstand multiple washings, and defines an inner surface adapted to be positioned against the skin of a baby and an outer surface. The cloth of the diaper further comprises a front portion, a back portion adapted to receive the buttocks of the wearer, and a connecting portion connecting the front portion and the back portion. The connecting portion is also adapted to extend between the legs of the wearer. The back portion further defines a pair of opposing laterally extending tabs which include fasteners secured to one of the front portion and back portion. The fasteners are adapted to connect the tabs to the front portion when the diaper is worn.

The preferred embodiment of the diaper uses a thermochromic ink, similar to the thermochromic ink of U.S. Pat. No. 4,826,550, assigned to Sakura Color Corporation, to provide the indication of a temperature change in the diaper.

Using conventional silk screening techniques applied to the thermochromic ink, a plurality of discrete indicators, such as small cartoon figures, are distributed over the outer surface of the diaper with the indicators forming a repeating pattern. Each of the plurality of indicators provides a visual indication when the outer surface has a temperature above a given threshold. Desirably, the indicators cover a significant portion of the outer shell of the diaper so that the wetness condition can be easily detected from most viewing angles of the diaper in an aesthetically pleasing manner.

The temperature threshold which results in a visual indication may advantageously be at temperatures above 60° F., is desirably above 70° F., is more desirably above 80° F. and preferably is above 87° F. Desirably, the visual indication of a change in temperature threshold is a change in color. The diaper desirably returns to its non-indicating color when the temperature of the diaper falls below the given threshold. The thermochromic ink that is screened onto the diaper may comprise a mixture of thermochromic inks or a single thermochromic ink depending on the type of color change that is desired. In one embodiment, the indicators may be visible when the outer surface has a temperature above a given threshold. In another embodiment, the indicators are not visible when then outer surface has a temperature above a given threshold. In still another embodiment, the indicators appear one color when the outer surface has a temperature above a given threshold and appear another color when the outer surface has a temperature below the threshold.

The present invention further comprises a method of detecting the wetness of a diaper having an inner surface, an outer surface and a thermal indicator. The method of detecting the wetness of a diaper comprises at least partially thermally insulating the inner surface of the diaper from the outer surface of the diaper, wicking any moisture from the inner surface towards the outer surface to bring the moisture into thermal contact with the thermal indicator, and providing a visual indication when the thermal indicator is exposed to a temperature above a given threshold.

DETAILED DESCRIPTION OF THE PREFERRED EMBODIMENT

Figure 1:
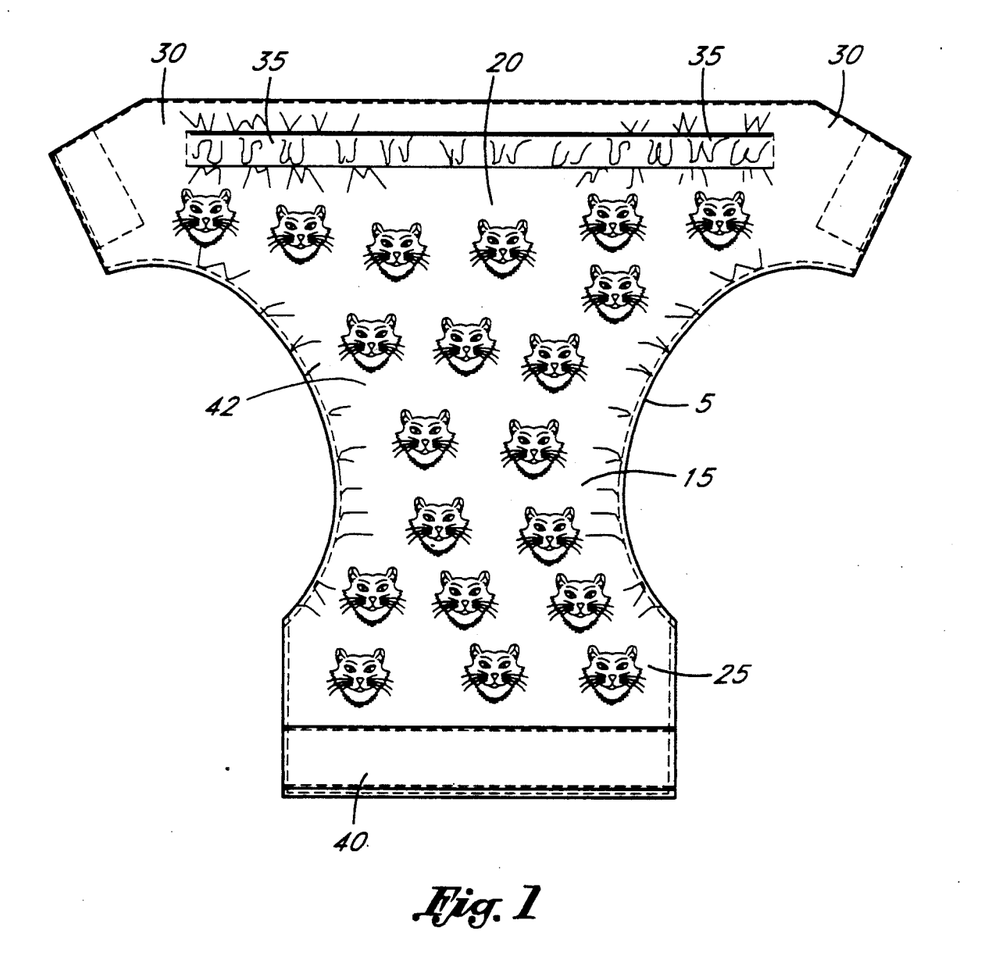
FIG. 1 is a bottom plan view of the preferred embodiment of the diaper of the present invention.
Figure 2:
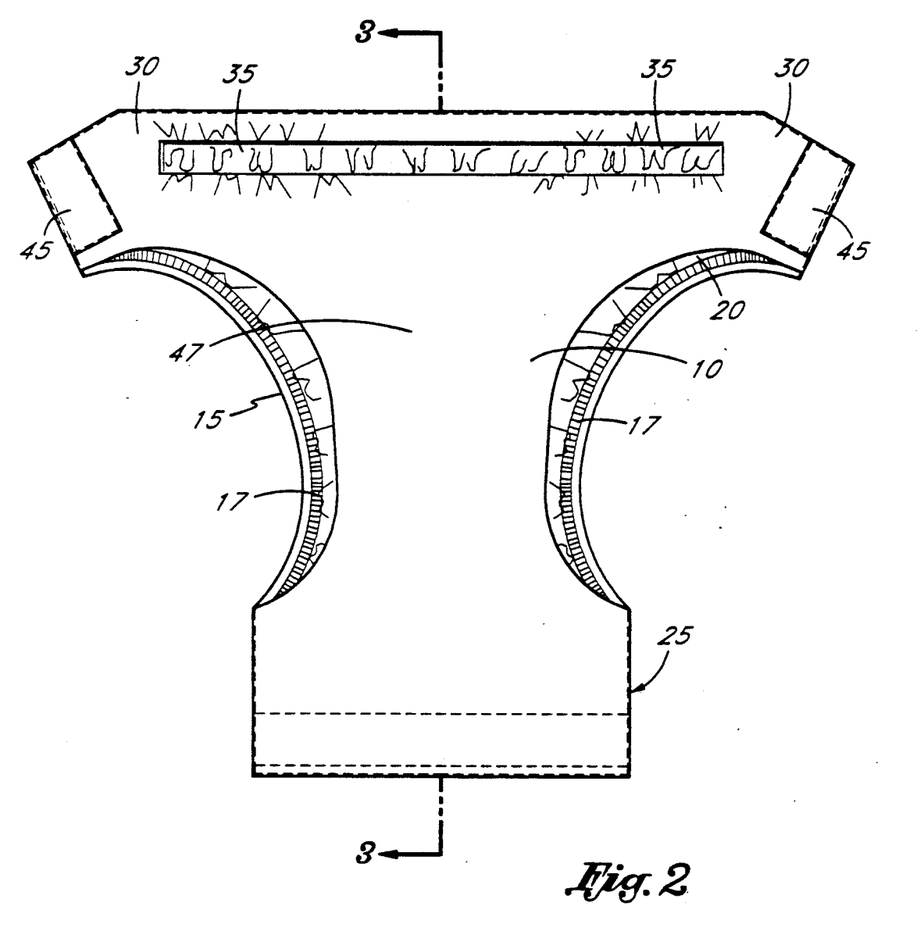
FIG. 2 is a top plan view of the preferred embodiment of the present invention.

FIGS. 1 and 2 illustrate a preferred embodiment of a reusable cloth diaper that indicates when a baby wearing the diaper is wet by detecting a change in temperature. The diaper comprises a substantially non-absorbent outer shell which is made from a durable soft fabric material, an inner pad and an indicator which provides visual indication when the outer shell of the diaper has a temperature above a given threshold. The threshold is chosen so that the visual indication is not present when the baby wearing the diaper is dry, and will be present when the baby secretes waste material into the diaper. The inner pad substantially absorbs the waste of the baby and provides a partially thermally insulating layer between the baby wearing the diaper and the outer shell of the diaper. The preferred embodiment of the invention utilizes a thermally sensitive ink to provide an indication of a wetness condition.

The preferred configuration of the diaper, comprises an outer shell 5 connected to an inner pad 10. The outer shell 5 further comprises a back portion 20, a front portion 25, and a connecting portion 15 that connects the front portion and the back portion of the diaper. The inner pad 10 is only connected to the outer shell 5 at the front 25 and back 20 portions of the outer shell 5. The connecting portion 15 of the diaper is substantially rounded to fit comfortably between the legs of an infant. The connecting portion 15 also includes a woven elastic band 17 sewn onto the outer shell 5 to gently hold the diaper onto the child's legs to prevent gaping of the diaper as the child moves.

The front portion 25 folds onto the stomach of the wearer while the back portion 20 of the diaper cradles the buttocks. The back portion also has a pair of opposing laterally extending tabs 30 which wrap around the child's sides to meet the front portion 25 of the diaper. In order to secure the diaper on the wearer, fasteners, such as hook and loop fasteners sold under the name "VELCRO", are attached to the front 25 and back 20 portions of the diaper to connect the tabs to the front portion 25 when the diaper is worn. An elastic band 35 is sewn onto the tabs 30 as the material of the tabs is gathered to form a stretchable waist band which can be adjusted to wrap around the sides of most children. The front portion 25 of the diaper preferably has a strip of the looped VELCRO fastener 40, style #71, attached to the outer surface 42 of the outer shell 5 of the diaper along the entire top of the front portion 25 of the diaper. Preferably, the two elasticized back tabs 30 each have a piece of the hooked VELCRO fasteners 45, style #704, sewn onto an inner surface 47 of the diaper.

When the elasticized tabs 30 of the back portion 20 of the diaper are stretched around the sides of the baby's waist, the hooked VELCRO fasteners 45 can attach to any location on the looped VELCRO fastener 40 along the front portion 25 of the diaper. Thus, the diaper can be used on various sizes of children by varying the amount of stretch that is required of the elasticized back tabs 30, and the location on the front looped fastener 40 that the hooked fasteners 45 on the back tabs 30 are attached.

Figure 3:
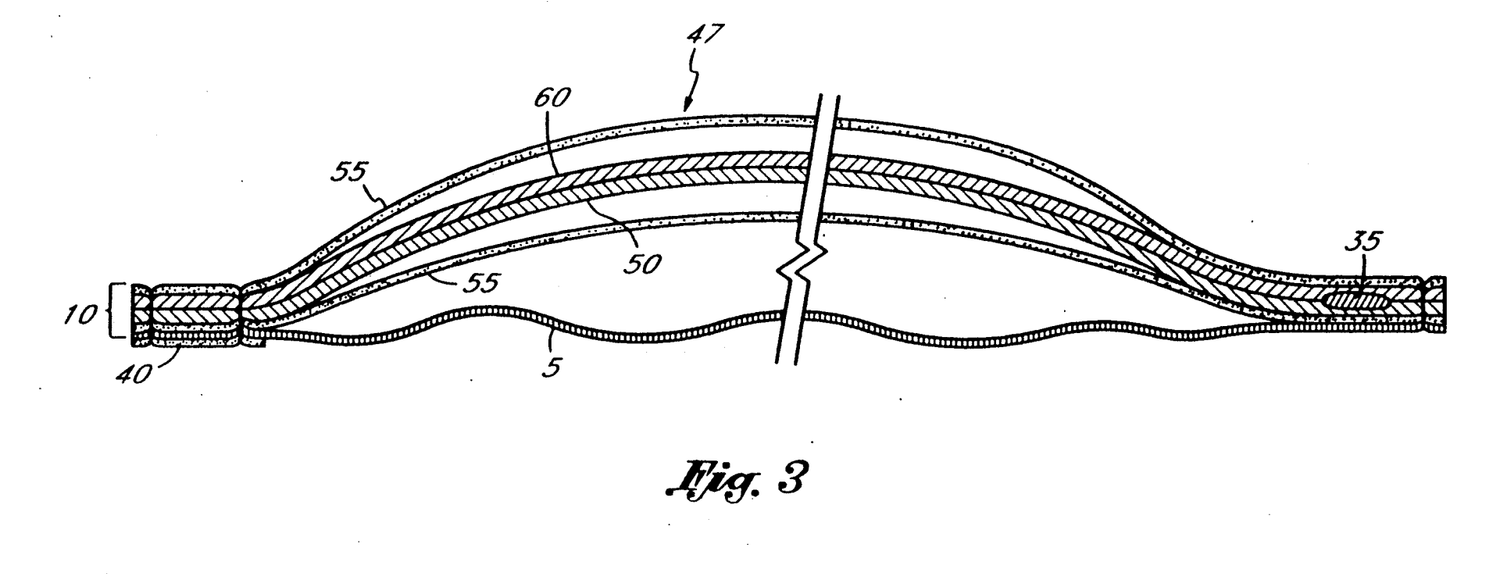
FIG. 3 is a cross-sectional view of the preferred embodiment of the present invention.

The diaper is preferably made from material that is sufficiently durable to withstand multiple washings. The outer shell 5 of the diaper is made from a substantially nonabsorbent material that provides a sturdy exterior of the diaper. The preferred embodiment of the outer shell 5 comprises Dupont style #22-2 material which is 97% Dacron and 6% Lycra. As illustrated in FIG. 3, the inner pad 10 preferably comprises multiple layers: a sorbent layer 50, a protective covering 55 and a layer of wicking material 60 between the protective covering 55 and the sorbent layer 50. The protective covering 55 defines the inner surface 47 of the diaper which is adapted to be positioned against the skin of the baby when the diaper is worn. The protective covering 55 further surrounds the sorbent layer 50 thereby separating the sorbent layer 50 from the outer shell 5. The inner pad 10 at least partially thermally insulates the inner surface 47 of the diaper from the outer shell 5. The preferred embodiment of the protecting covering 55 comprises a layer of BIRD'SEYE 100% cotton which is soft and substantially non-irritating to the skin of the infant wearing the diaper. The preferred embodiment of the sorbent layer 50 comprises looped terry 100% cotton having a thickness of at least ¾ of an inch, and the preferred embodiment of the wicking layer 60 comprises Du Pont style #1178B (poly thyon) material. The wicking layer 60 draws the moisture away from the baby's buttocks to the sorbent layer 50. The wicking layer 60 not only removes the wetness from the baby's buttocks and provides greater comfort for the child, but by quickly wicking the wetness to the sorbent layer, it quickly brings the waste into thermal contact with the heat sensitive ink on the outer shell 5 of the diaper.

As stated above, the preferred embodiment of the present invention is designed to be extremely durable. The materials that were chosen can be washed and dried several times, and still be in a condition for repeated use. In order to wash the diaper, the diaper is turned inside out so the hooked VELCRO fasteners 45 on the extended tabs 30 are between the outer shell 5 and the inner pad 10. By turning the diaper inside out, the hooked VELCRO fasteners 45 are no longer able to come into contact with or snag any article that the diaper is being washed with. Further, by turning the diaper inside out the drying time of the diaper is reduced by ⅓ of the normal rate.

Another feature that reduces drying time is the manner in which the inner pad 10 is connected to the outer shell 5. The inner pad 10 and the outer shell 5 of the diaper are only attached at the front 25 and back 20 portions of the outer shell 5, therefore the inner pad 10 of the diaper is free to move independently from the outer shell 5 of the diaper. This independent movement of the inner pad 10 from the outer shell 5 allows air to pass between the inner pad 10 and the outer shell 5 to ventilate the diaper which assists in reducing the drying time. More importantly, this ventilation allows the heat from the child's body to escape from the diaper and helps prevent the heat sensitive wetness indicating ink from changing color when the diaper is not wet. The inner pad 10 of the diaper is designed for optimal thickness to insulate the child's body temperature from the outer shell 5 of the diaper, while still allowing the wetness to be drawn to the outer shell 5 by the wicking layer 60 and effectuate the color change in the thermal sensitive ink when the diaper is soiled.

The outer shell 5 of the diaper is screened using conventional silk screening techniques to screen a repeating pattern, such as several small cartoon figures, covering substantially the entire outer surface of the diaper using the thermally sensitive ink. The thermally sensitive ink is designed to change color when the heat from the wet and soiled diaper reaches the outer shell of the diaper. Therefore, the color of the thermally sensitive pattern, i.e. the cartoon figures, will change when the diaper becomes wet. This is much more aesthetically pleasing than the spot indicators of the prior art. In addition, the repeated pattern is desirably placed over substantially the entire outer surface 42 of the outer shell 5 of the diaper; therefore, from virtually any angle there will be an indicating means available to the parent to determine if the diaper is wet.

The thermally sensitive ink used is desirably a thermochromic ink. The thermochromic ink is an organic compound that effectuates the reversible color change when a specific temperature threshold is crossed. The thermochromic ink that is used is similar to the thermochromic ink of U.S. Pat. No. 4,826,550, assigned to Sakura Color Corporation, and which is hereby incorporated by reference.

The basic composition of the thermochromic color changeable ink consists of three components which perform the following functions: (1) an electron donating coloring organic compound for determining the color, (2) an electron accepting compound for determining the concentration of the color, and (3) a fatty acid for determining the color-change temperature. The mechanism that causes the color change to occur is described in Table 1 below:

TABLE 1

| Composition | Function | Heat sensitive paper Pressure sensitive paper colorless $\xrightarrow{\text{heat, pressure}}$ color | Reversible heat sensitive ink color $\underset{\text{cool}}{\overset{\text{heat}}{\rightleftarrows}}$ colorless |
|---|---|---|---|
| Coloring matter | determining the color | Electron donating color organic compound (leuco dye) (pressure sensitive dye) (heat sensitive dye) | Electron donating coloring organic compound (leuco dye) (pressure sensitive dye) |
| Color developing matter | giving color to coloring matter | Phenol compound Acid clay | Phenol compound Triazole compound |
| Desensitizer | determining the discoloring temperature | X | Alcohol, fatty acid Amido compound Ester compound |

Although it is not entirely clear why the above composition is subject to thermochromism, it is generally understood as thermal equilibrium of an electron movement.

In order to control the temperature at which the color change occurs different types of fatty acids are used. The discoloring temperature corresponds to the fusing temperature of a fatty acid. The fatty acid will change from a solid state to a liquid state when heated, therefore when the thermochromic ink is heated the fatty acid will change state and effectuate the color change. As the thermochromic ink cools, the fatty acid will solidify and return the ink to its original color. Further, it is possible to minutely regulate the discoloring temperature by using two or more kinds of fatty acids mixedly. Table 2 shows different fatty acids and their respective transition temperatures.

TABLE 2

| FATTY ACID | | transition temp. (°C.) |
|---|---|---|
| capric acid | (carbon No. 10) | 31 |
| lauric acid | 12 | 44 |
| myristic acid | 14 | 53 |

TABLE 2-continued

| FATTY ACID | | transition temp. (°C.) |
| --- | --- | --- |
| palmitic acid | 16 | 63 |
| stearic acid | 18 | 69 |
| behenic acid | 22 | 79 |

In order to determine the color of the thermochromic ink, different electron donating compounds are used. The electron donating coloring organic compound is colorless in its simple substance. However, when coming into contact with an electron accepting compound such as solid acid, the electron donating coloring organic compound exhibits color. Specifically, names of electron donating coloring organic compound and their hues are:

| | |
| --- | --- |
| 3.6-dimethoxyfluoran | yellow |
| 3-cyclohexylamino-6-chlorofluoran | orange |
| 3-diethylamin-6-methyl-7-chlorofluaran | vermilion |
| 3-diethylaminobenzfluoran | pink |
| rhodamine B lactam | red |
| crystal violet lactone | blue |
| 3-diethylamino-7-dibenzylaminofluoran | green |
| 3-diethylamino-6-methyl-7-anilinofluoran | black |

Further, if these compounds are mixed, their mixed colors can also be obtained. In fact, these coloring matters are used for pressure sensitive copy paper, heat sensitive recording paper and the like. The use of these coloring matters is prevalent in our daily life.

On the other hand, phenols are used as electron accepting compounds. An example of general composition of thermochromic ink is:

| | |
| --- | --- |
| 1) Coloring matter | 1 group |
| 2) Phenols | 5 groups |
| 3) Fatty acids | 50 groups |

Thermochromic (TC) ink depends on the balance of composition of the aforementioned three components. In the case where the balance of composition is lost through the repeating process of exhibiting and disappearing color, thermochromic ink can no longer discolor to the set color at the set discoloring temperature. Particularly, the fatty acid which determines the discoloring temperature exhibits and disappears the color by changing from the solid to the liquid or vice versa. Accordingly, the fatty acid, in its liquid state, is liable to move outside the system.

Therefore, the composition of the three components is required to be encapsulated in a microcapsule. This technique is referred to as microencapsulation, and is necessary for putting the thermochromic ink into practical use.

Various methods of microencapsulation are known in the art, some of which are set forth in Table 3. However, since fatty acids have a high chemical activity, the usable microencapsulation methods are very limited.

TABLE 3

| Methhold of Encapsulation and Its Classification | |
| --- | --- |
| Classification by encapsulation process | Method of encapsulation |
| 1. Chemical method | (1) Method by interfacial reaction<br>Interfacial polymerization<br>(2) In-situ polymerization<br>(3) Hardening and coating in liquid<br>· Dispersing Method<br>Orifice Method |
| 2. Physical and chemical method | (1) Coacervation (phase separation) from aqueous solution<br>Simple coacervation<br>Compound coacervation<br>(2) Coacervation from organic solution<br>By changing temperature<br>By adding insoluble solvent<br>By adding inductive agent for phase separation<br>(3) Drying method in liquid<br>(4) Melting and cooling method<br>(5) Exchanging internal phase |
| 3. Mechanochemical and physical method | (1) Wurster method<br>(2) Spray drying<br>(3) Mechanochemical method (mixing powder)<br>(4) Vacuum deposition coat<br>(5) Electrostatic coat<br>(6) By shocking in high speed air current |

At present, thermochromic ink is made with microencapsulation that is effected by the In-situ polymerization with urea formalin resin used as wall material.

In this way, three components encapsulated in the microcapsule are used as primary material for thermochromic ink. Since microencapsulation is to be effected in the liquid phase, the primary material for thermochromic ink is in a water disperse state containing about 45% wt. of capsule particles. The capsulated thermochromic ink when dispersed in water containing the 45% wt. of capsule particles is called a TC slurry. The TC slurry is blended with water base binders at a ⅔ ratio respectively to form the thermochromic water-based ink used in the present invention.

Thus, the thermochromic ink used in the present invention provides the following advantages:

(1) The choice of a desired color, e.g., orange, pink, red, purple, blue, green, and black;

(2) The free setting of a discoloring temperature in the temperature range of −30° C. to +80° C.;

(3) Basic color changes from color to colorless and vice versa;

(4) By blending the coloring matter which are not to discolor according to the temperature change, the color change can be designed so as to discolor from color A to color B and vice versa;

(5) Sensitivity of discoloration has a range of ±1° to 2° C., but sensitivity of the temperature is slightly inferior to that of liquid crystal;

(6) Repeatability of the color change, potentially tens of thousands of times. However, it is expected that the use of discoloration may not be repeated as many times depending upon how the heat is applied.

The thermochromic ink that is used in the preferred embodiment of the present invention provides an indication of wetness when the temperature of the ink exceeds a specific threshold. It has been determined that the temperature threshold is advantageously about 60° F., is desirably above 70° F., is more desirably above 80° F. and is preferably above 87° F. for the indicators of the present invention. The indicator advantageously returns to its normal color when the temperature falls below the specified threshold temperature. In one embodiment of the present invention, the ink that is screened onto the preferred embodiment of the diaper is a mixture of two thermochromic inks, one of which becomes colorless at temperatures above the specified threshold value. Thus, the indication of wetness occurs when one of the two thermochromic inks of the preferred embodiment becomes colorless, and thereby effectuates the color change. In an alternate embodiment of the present invention, the diaper is screened using a thermochromic ink that is colorless below a given threshold temperature, and is colorful above a given threshold level. In this embodiment the indicators are colorful when the diaper is wet, and are colorless when the diaper is dry. In a further embodiment of the present invention, the diaper is screened using a thermochromic ink that is colorless above a given threshold temperature, and is therefore colorful below the given threshold level. In this further embodiment, the indicators are colorless when the diaper is wet, and are colorful when the diaper is dry.

As described above, the heat sensitive thermochromic ink will change colors when the dye reaches the color change threshold temperature. In previous applications of thermochromic dyes on clothing, it was desirable to effectuate the color change when the wearer of the garment became hot. In this case, it is only desirable to have a color change when the infant soils his diapers, not when the infant becomes hot. In order to prevent undesired color change, the inner pad 10 of the diaper is designed to insulate the baby's skin temperature from contacting the outer shell 5 where the heat sensitive dye is located, while still allowing the wetness to be drawn into thermal contact with the outer shell 5 and effectuate the color change in the thermal sensitive ink. The material of the inner pad 10 is insufficiently thermally conductive for a normal body temperature to raise the outer surface above a given threshold, but is sufficiently thermally conductive when wet to raise the outer surface temperature above a given threshold. This thickness of the inner pad 10 is therefore at least ⅜ of an inch thick. The insulative property of the diaper that prevents the heat from the baby's skin to cause a false color change is therefore based on the effectiveness of the insulative material as well as the thickness of the layers of material that comprises the inner pad 10.

In addition, by screening the thermochromic inks onto the garment in a repeated pattern, such as a cartoon type design, it allows the color change to be limited to a controlled area. Several prior art applications of the thermochromic inks were used on the entire garment or a significant portion of the garment. This would not be desirable for use on diapers because when the child wets his diaper the garment would change colors along the entire soiled area of the garment. This would result in an unattractive blotch of the changed color. In contrast, the design of the present invention allows for the coverage of substantially the entire outer shell 5 of the diaper with the indicating ink, yet limits the area of the color change to an appealing pattern or figure.

In addition, the thermochromic screened ink is a durable indicator which can be washed repeatedly with various laundry detergents and dried in a hot dryer, and continue to properly indicate diaper wetness. The prior art wetness indicating diapers have not provided the durability of the present invention and therefore did not provide the market with a functional nor practical design.

In addition, the diaper of the present invention is reusable, and therefore a recyclable product. As the land fills in our country become full, mostly due to the amount of disposable diapers that are throw away each year, the need for a better reusable diaper will continue to grow. The wetness indicating diaper is designed to make the use of cloth diapers easier, and more appealing to the marketplace.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

I claim:
1. A diaper for indicating wetness, comprising:
an inner surface adapted to be positioned against the skin of a baby;
an outer surface generally opposed to said inner surface adapted to form the exterior of said diaper;
material positioned between said interior and exterior surfaces, which, when dry is insufficiently thermally conductive for a normal body temperature to raise said outer surface above a given threshold, but being sufficiently thermally conductive when wet to raise said outer surface temperature above a given threshold, at least partially thermally insulates said outer surface from said inner surface;
a thermal indicator on said outer surface which provides a visual indication when said outer surface has a temperature above a given threshold; and said threshold being chosen such that said visual indication will generally not be present when a baby wearing said diaper is dry, but will generally be present when said baby secretes waste material into said diaper.

2. The diaper of claim 1, wherein said material wicks moisture secreted from said baby toward said outer layer.

3. The diaper of claim 1, wherein said threshold is above 60 degrees Fahrenheit.

4. The diaper of claim 1, wherein said threshold is above 70 degrees Fahrenheit.

5. The diaper of claim 1, wherein said threshold is above 80 degrees Fahrenheit.

6. The diaper of claim 1, wherein said threshold is above 87 degrees Fahrenheit.

7. The diaper as in any of claims 1-5, wherein said thermal indicator is no longer visible when said outer shell has a temperature which falls below said threshold.

8. The diaper of claim 7, wherein said thermal indicator comprises thermochromic ink.

9. The diaper of claim 8, wherein said thermal indicator comprises a mixture of thermochromic inks, one of which becomes colorless above said threshold.

10. A diaper for indicating wetness, comprising:
an outer shell having a front portion, a back portion and a connecting portion extending between said front and back portions;
an inner pad attached to said outer shell solely at said front portion and said back portion, said inner pad defining an inner surface adapted to be positioned against the skin of a baby when said diaper is worn, said inner pad, when dry, at least partially thermally insulating said inner surface from said outer shell;
a thermal indicator on said outer shell which provides a visual indication when said outer shell has a temperature above a given threshold, said threshold being chosen such that said visual indication will generally not be present when a baby wearing said diaper is dry, but will generally be present when said baby secretes waste material into said diaper.

11. The diaper of claim 10, wherein said inner pad includes a sorbent layer.

12. The diaper of claim 11, wherein said sorbent layer is protected by a cover, said protective cover forming said inner surface of said diaper.

13. The diaper of claim 12, wherein said protective cover surrounds said sorbent layer so as to separate said sorbent layer from said outer shell.

14. A diaper for indicating wetness, comprising:
an outer shell having a front portion, a back on and a connecting portion extending between said front and back portions;
an inner pad, comprising:
a sorbent layer;
a protective cover defining an inner surface of said diaper; and,
a layer of wicking material between said protective cover and said sorbent layer; and,
a thermal indicator on said outer shell which provides a visual indication of wetness when said outer shell has a temperature above a given threshold.

15. The diaper of claim 14, wherein said protective cover surrounds said sorbent layer, thereby separating said sorbent layer from said outer shell.

16. The diaper of claim 14, wherein said inner pad has a thickness of at least ¾ of an inch.

17. A diaper for indicating wetness, comprising:
an inner surface adapted to be positioned against the skin of a baby;
an outer surface generally opposed to said inner surface adapted to form the exterior of said diaper;
a layer positioned between said inner and outer surface providing at least some thermal insulation capacity when dry and a lower thermal insulation capacity when wet; and,
a thermal indicator on said outer surface which provides a visual indication when said outer surface has a temperature above a given threshold.

18. A diaper for indicating wetness, comprising:
a cloth sufficiently durable to withstand multiple washings, said cloth defining an inner surface adapted to be positioned against the skin of a baby and an outer surface, said cloth comprising:
a front portion;
a back portion adapted to receive the buttocks of the wearer, said back portion defining a pair of opposing laterally extending tabs; and,
a connecting portion connecting said front portion and said back portion adapted to extend between the legs of the wearer;
fasteners secured to one of said front portion and said back portion adapted to connect said tabs to said front portion when said diaper is worn; and,
a plurality of discrete thermal indicators distributed over substantially the entire outer surface of said diaper, each of said plurality of internal indicators providing a visual indication of wetness when said outer surface has a temperature above a given threshold.

19. The diaper of claim 18, wherein said thermal indicators form a repeating pattern.

20. The diaper of claim 18, wherein said thermal indicators are visible when said outer surface has a temperature above a given threshold.

21. The diaper of claim 18, wherein said thermal indicators are not visible when said outer surface has a temperature above a given threshold.

22. The diaper of claim 18, wherein said thermal indicators appear one color when said outer surface has a temperature above a given threshold and appear another color when said outer surface has a temperature below said threshold.

23. A method of detecting the wetness of a diaper having an inner surface, an outer surface and a thermal indicator, comprising:
at least partially thermally insulating said inner surface of said diaper from said outer surface of said diaper;
wicking any moisture from said inner surface towards said outer surface to bring said moisture into thermal contact with said thermal indicator; and,
providing a visual indication when said thermal indicator is exposed to a temperature above a given threshold.

* * * * *

UNITED STATES PATENT AND TRADEMARK OFFICE
CERTIFICATE OF CORRECTION

PATENT NO. : 5,197,958
DATED : March 30, 1993
INVENTOR(S) : Wesley A. Howell

It is certified that error appears in the above-indentified patent and that said Letters Patent is hereby corrected as shown below:

In Column 11, Line 33, change "a back on" to -- a back portion--.

In Colum 12, Lines 1 and 2, change "surface" to --surfaces--.

In Column 12, Line 25, change "internal indicators" to --thermal indicators--.

Signed and Sealed this

Twelfth Day of July, 1994

Attest:

BRUCE LEHMAN

*Attesting Officer*  *Commissioner of Patents and Trademarks*